(12) United States Patent
Jiang et al.

(10) Patent No.: US 7,393,674 B2
(45) Date of Patent: Jul. 1, 2008

(54) THROMBIN COMPOSITIONS

(75) Inventors: Shan Jiang, Sammamish, WA (US); Richard I. Senderoff, Edmonds, WA (US); Jeffrey D. Meyer, Lake Forest Park, WA (US)

(73) Assignee: Zymogenetics, Inc., Seattle, WA (US)

( * ) Notice: Subject to any disclaimer, the term of this patent is extended or adjusted under 35 U.S.C. 154(b) by 203 days.

(21) Appl. No.: 11/157,707

(22) Filed: Jun. 21, 2005

(65) Prior Publication Data

US 2006/0002918 A1 Jan. 5, 2006

Related U.S. Application Data

(60) Provisional application No. 60/581,824, filed on Jun. 22, 2004.

(51) Int. Cl.
*C12N 9/74* (2006.01)

(52) U.S. Cl. .................. 435/214; 435/7.1; 530/300; 530/350

(58) Field of Classification Search .............. None
See application file for complete search history.

(56) References Cited

U.S. PATENT DOCUMENTS

| | | | | |
|---|---|---|---|---|
| 4,363,319 A | | 12/1982 | Altshuler | 604/304 |
| 4,696,812 A | | 9/1987 | Silbering et al. | 424/445 |
| 4,923,815 A | | 5/1990 | Tanaka et al. | 435/183 |
| 5,130,244 A | | 7/1992 | Nishimaki et al. | 435/188 |
| 5,281,528 A | * | 1/1994 | Boctor et al. | 435/212 |
| 5,354,682 A | | 10/1994 | Kingdon et al. | 435/214 |
| 5,484,913 A | | 1/1996 | Stilwell et al. | 536/57 |
| 5,645,849 A | | 7/1997 | Pruss et al. | 424/426 |
| 5,981,254 A | | 11/1999 | Bui-Khac | 435/214 |
| 6,280,727 B1 | | 8/2001 | Prior et al. | 424/94.63 |
| 6,310,183 B1 | * | 10/2001 | Johannessen et al. | 530/384 |
| 2005/0232899 A1 | | 10/2005 | Balwani et al. | 424/85.7 |

FOREIGN PATENT DOCUMENTS

| | | |
|---|---|---|
| EP | 0 505 604 | 9/1992 |
| EP | 1 221 479 | 7/2002 |

OTHER PUBLICATIONS

Carpenter et al., "Rational Design of Stable Lyophilized Protein Formulations: Some Practical Advice," Pharmaceutical Research 14(8): 969-975, 1997.
Carpenter et al., "Ch. 5: Rational Design of Stable Lyophilized Protein Formulations: Theory and Practice," pp. 109-133, in *Rational Design of Stable Protein Forumlations*, Carpenter and Manning (eds.), Kluwer Academic / Plenum Publishers, New York, 2002.
Cleland et al., "A Specific Molar Ratio of Stabilizer to Protein is Required for Storage Stability of a Lyophilized Monoclonal Antibody," Journal of Pharmacuetical Sciences 90(3):310-321, Mar. 2001.
Johnson et al., "Mannitol—Sucrose Mixtures- Versatile Formulations for Protein Lyophilization," Journal of Pharmaceutical Sciences, 91(4): 914-922, Apr. 2002.
Jones Pharma Incorporated, Thrombin, Topical U.S.P.s, Sep. 2000.
Kolodzeyskaya and Chernyshenko, "Experimental Works," Ukr. Biochem. Journ. 74(5): 27-33, 2002. (Translation attached).
Le Borgne and Graber, "Amidase Activity and Thermal Stability of Human Thrombin," Applied Biochemistry and Biotechnology 48: 125-135, 1994.

* cited by examiner

*Primary Examiner*—Hope A Robinson
(74) *Attorney, Agent, or Firm*—Zgen IP Dept.; Jeff Landes

(57) ABSTRACT

Compositions comprising thrombin and methods of preparing them are disclosed. The composition may be in the form of an aqueous solution at pH 5.7-7.4 consisting essentially of 0.1 mg/mL to 5.0 mg/mL thrombin, 2% to 4% (w/v) sucrose, 3.5% to 5% (w/v) mannitol, 50 mM to 300 mM NaCl, 0-5 mM $CaCl_2$, 0.03% to 1% (w/v) of a surfactant or high-molecular-weight polyethylene glycol, and a physiologically acceptable buffer, or may be in lyophilized form.

27 Claims, 5 Drawing Sheets

THROMBIN COMPOSITIONS

CROSS-REFERENCE TO RELATED APPLICATION

This application claims the benefit of U.S. Provisional Application Ser. No. 60/581,824, filed Jun. 22, 2004, which is herein incorporated by reference.

BACKGROUND OF THE INVENTION

Formulation of pharmaceutical proteins presents significant challenges. Proteins possess multiple functional groups in addition to three-dimensional structure; degradation therefore proceeds via both chemical (modifications involving bond formation or cleavage) and physical (denaturation, aggregation, adsorption, precipitation) pathways. Since each protein embodies a unique combination of amino acid sequence, isoelectric point, and other determinants, its response to changes in solution conditions is unpredictable, and must be determined on a case-by-case basis. Attempts to prevent one form of degradation often increase the rate of another.

Degradation of proteins can be greatly reduced or avoided by lyophilization. However, lyophilization is time-consuming and costly, and can cause protein denaturation and aggregation if appropriate excipients are not included. As with solution formulation, stabilization of lyophilized proteins must be dealt with on an individual basis.

In the case of thrombin, sodium chloride can be used to maintain stability during purification and storage by reducing aggregation and precipitation. However, sodium chloride is a problematic excipient in lyophilized formulations because it lowers glass transition temperature, thereby necessitating low primary temperatures and long cycle times. In addition, thrombin must be protected from unfolding and aggregation within the lyophilized composition.

The ideal formulation will combine stability during lyophilization, as well as long-term storage and shipment with ease of handling and use.

DESCRIPTION OF THE INVENTION

Within one aspect of the invention there is provided a composition consisting essentially of 0.1 mg/mL to 5.0 mg/mL thrombin, 2% to 4% (w/v) sucrose, 3.5% to 5% (w/v) mannitol, 50 mM to 300 mM NaCl, 0-5 mM $CaCl_2$, 0.03% to 1% (w/v) of a surfactant or high-molecular-weight polyethylene glycol, and a physiologically acceptable buffer, in aqueous solution at pH 5.7-7.4, wherein concentration of the buffer is selected to provide approximately physiological pH upon application of the composition in a surgical setting and wherein the ratio of mannitol:sucrose is greater than 1:1 but not greater than 2.5:1 (w/w). Within one embodiment of the invention the ratio of mannitol to sucrose is 1.33:1 (w/w). Within other embodiments of the invention the molar ratio of sucrose:thrombin is at least 700:1 or at least 2000:1. Within further embodiments of the invention the thrombin is human thrombin, including, for example, recombinant human thrombin. Within still other embodiments of the invention, the thrombin concentration is 0.5-3.0 mg/ml or the thrombin concentration is 1 mg/ml. Within other embodiments of the invention, the sucrose concentration is 3% (w/v) and/or the mannitol concentration is 4% (w/v). Within a further embodiment the surfactant or high-molecular-weight polyethylene glycol is PEG 3350. Within a related embodiment the surfactant or high-molecular-weight polyethylene glycol is PEG 3350 at a concentration of 0.1% (w/v). Within additional embodiments, the pH of the composition is 6.0. Within further embodiments the buffer is selected from the group consisting of histidine, citrate, phosphate, Tris, and succinate buffers. Within related embodiments the buffer is histidine buffer, such as 2.0-10 mM histidine buffer or 5 mM histidine buffer. One such composition of the present invention consists essentially of 0.1 mg/mL to 5.0 mg/mL thrombin, 2% to 4% (w/v) sucrose, 3.5% to 5% (w/v) mannitol, 100 mM to 200 mM NaCl, 1 mM to 5 mM $CaCl_2$, 0.03% to 1% (w/v) PEG3350, and 2 mM to 10 mM histidine in aqueous solution at pH 5.5-6.5, wherein the ratio of mannitol:sucrose is greater than 1:1 but not greater than 2.5:1 (w/w). A second such composition of the invention consists essentially of 1 mg/ml thrombin, 3% (w/v) sucrose, 4% (w/v) mannitol, 4 mM $CaCl_2$, 0.1% (w/v) PEG3350, 150 mM NaCl, and 5 mM histidine in aqueous solution at pH 6.0.

Within a second aspect of the invention there is provided a method of preparing a lyophilized thrombin composition comprising (a) providing an aqueous, thrombin-containing composition as disclosed above and (b) lyophilizing the aqueous composition to form a lyophilized thrombin composition.

Within a third aspect of the invention there is provided a lyophilized thrombin composition prepared by the method disclosed above. Within one embodiment of the invention the lyophilized composition is contained in a sealed container having a label affixed to an exterior surface thereof. Within an additional embodiment of the invention the composition in the sealed container contains from 2,500 to 20,000 NIH units of thrombin. Within a related embodiment of the invention the composition is provided in the form of a kit comprising a sealed container as disclosed above and a second sealed container containing a diluent such as, for example, normal saline.

These and other aspects of the invention will become evident upon reference to the following detailed description of the invention and the attached drawings.

Figure 1:
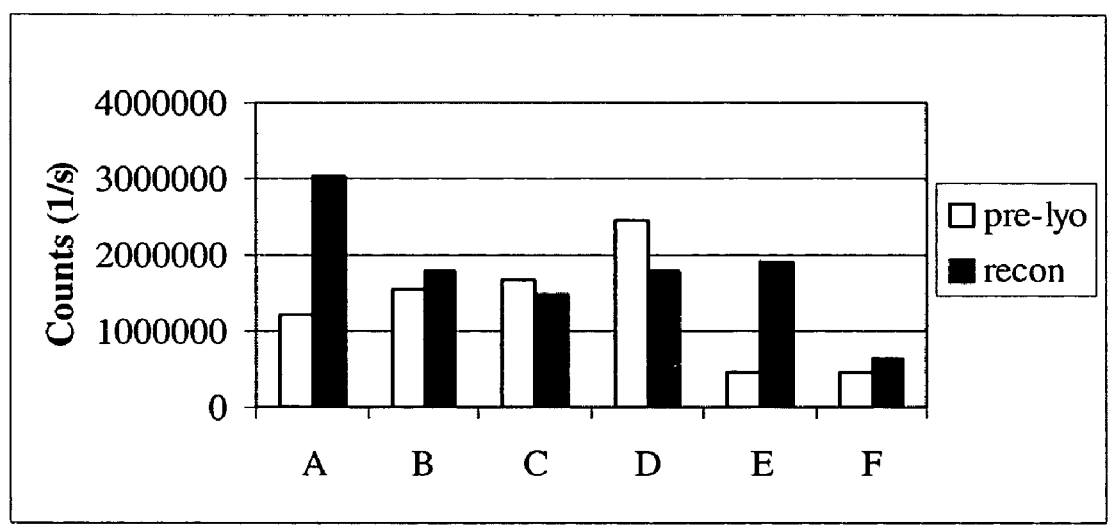
FIG. 1 illustrates the analysis of pre- and post-lyophilization samples of certain thrombin formulations by Right Angle Light Scattering (RALS).

All references cited herein are incorporated by reference in their entirety.

Numerical ranges (e.g., "from X to Y") include the endpoints unless otherwise specified.

The present invention provides stabilized thrombin compositions, including lyophilized compositions. As used herein, "thrombin" denotes the activated enzyme, also known as α-thrombin, which results from the proteolytic cleavage of prothrombin (factor II). As disclosed below, thrombin can be prepared by a variety of methods known in the art, and the term "thrombin" is not intended to imply a particular method of production. Human thrombin is a 295 amino acid protein composed of two polypeptide chains joined by a disulfide bond. Both human and non-human thrombins can be used within the present invention. Thrombin is used medically as a hemostatic agent and as a component of tissue adhesives.

Human and non-human (e.g., bovine) thrombins are prepared according to methods known in the art. Purification of thrombin from plasma is disclosed by, for example, Bui-Khac et al., U.S. Pat. No. 5,981,254. Purification of thrombin from plasma fractions, such as Cohn fraction III, is disclosed by Fenton et al., *J. Biol. Chem.* 252:3587-3598, 1977. Recombinant thrombin can be prepared from a prethrombin precursor by activation with a snake venom activator as disclosed in U.S. Pat. No. 5,476,777. Suitable venom activators include ecarin and prothrombin activator from *Oxyuranus scutellatus*.

Within the present invention, thrombin is formulated in a weakly buffered, aqueous solution containing sucrose, mannitol, sodium chloride, a surfactant or high molecular weight polyethylene glycol (HMW-PEG), and, optionally, calcium chloride. Concentration ranges of these components are shown in Table 1. Concentrations expressed as percent are on a weight-to-volume basis.

TABLE 1

| thrombin | 0.01-5.0 mg/mL |
|---|---|
| sucrose | 2%-4% |
| mannitol | 3.5%-5% |
| NaCl | 50-300 mM |
| surfactant or HMW-PEG | 0.03%-1% |
| $CaCl_2$ | 0-5 mM |
| pH | 5.7-7.4 |

The concentration of thrombin within the formulation of the present invention can be varied depending on the intended use, including the desired concentration of the reconstituted product. Thrombin is included in the formulation at a concentration of 0.01-5.0 mg/mL, more commonly 0.1-5.0 mg/mL, and typically 0.5-3.0 mg/mL. Within certain embodiments of the invention the concentration of thrombin is 1.0 mg/mL.

The inventors have found that the ratio of mannitol to sucrose significantly affects protein unfolding during lyophilization. Mannitol is included as a bulking agent, to improve lyophilization cycle efficiency and lyophilized product appearance. Sucrose is included as a stabilizer (lyoprotectant), reducing thrombin unfolding during lyophilization and upon storage. Formulations having a mannitol:sucrose ratio of 5:1 (w/w) or greater were unacceptable; those having a ratio of 2.5:1 or less appeared stable as analyzed by Fourier transform infrared spectroscopy (FTIR). Ratios of 1:1 or less showed aggregation/precipitation in solution (upon reconstitution) as measured by right angle light scattering (RALS) and did not form an acceptable cake upon lyophilization. Thus, within the present invention the ratio of mannitol:sucrose will be greater than 1.1 but not greater than 2.5:1.

NaCl is included in the formulation to reduce aggregation and/or precipitation. As noted above, NaCl can be problematic in the lyophilization process. Within the formulation of the present invention, NaCl is included at a concentration of 50 mM to 300 mM. Within certain embodiments of the invention the concentration of NaCl is 75 mM to 250 mM, 100 mM to 200 mM, or 150 mM.

The thrombin formulation of the present invention is buffered to provide for stability during formulation and to optimize activity upon reconstitution. While not wishing to be bound by theory, it is believed that autolytic degradation of thrombin increases as pH increases above 6.0, and the precipitation rate increases as pH decreases below 6.0. It is therefore desirable to prepare thrombin at slightly acidic to approximately neutral pH to limit loss of activity due to autolysis (formation of inactive autolytic degradation products including β- and γ-thrombin). However, to provide optimal biological activity upon use, approximately physiological pH is desired. The present invention addresses these conflicting needs through the use of a weak buffer that is effective at slightly acidic to approximately neutral pH (i.e, pH 5.7-7.4), but will allow the pH to reach approximately physiological pH (i.e., pH 6.8-7.5, preferably pH 7.0-7.5, more preferably pH 7.35-7.45) when the thrombin is applied to bleeding tissue in a surgical setting. Within the present invention the thrombin solution is buffered at pH 5.7-7.4, commonly 6.0-6.5, and, within certain embodiments, 6.0. Suitable buffers include, in addition to histidine, other physiologically acceptable buffers that are effective within the noted pH range and will allow the solution to reach approximately physiological pH upon application of the composition in a surgical setting. Examples of such buffers include phosphate, citrate, Tris (2-Amino-2-(hydroxymethyl)-1,3-propanediol), and succinate. Within certain embodiments of the invention, histidine buffer is included at 1-20 mM, 2-10 mM, or 5 mM.

Suitable concentrations of other buffers within the present invention can be readily determined by one of ordinary skill in the art. Formulation buffers can be tested by adding blood and measuring the pH of the resulting solution. In an exemplary assay, aliquots of rabbit blood are added stepwise to various buffers, and pH is measured after each addition. When histidine buffers are tested in such an assay, 3.2 mM, 5 mM, 12.8 mM, and 20 mM histidine are neutralized by the addition of not more than 1.0 volume of blood. In contrast, 160 mM succinate buffer and 90 mM phophate/12.8 mM histidine buffer did not produce a mixture with a pH above 7.0 even after addition of 2-3 volumes of blood.

Within the present invention, a surfactant or high-molecular-weight polyethylene glycol (PEG) is included to prevent adsorptive losses and shear-induced thrombin aggregation/precipitation in solutions prior to lyophilization or after reconstitution of the lyophilized product. Suitable surfactants useful in this regard include polyethylene oxides, sorbitan esters, polyoxyethylene alkyl ethers, glycerides of fatty acids (e.g., glyceryl monooleate and glyceryl monostearate), polyoxyethylene sorbitan fatty acid esters (e.g., polysorbate 20 (polyoxyethylene sorbitan monolaurate) and polysorbate 80 (polyoxyethylene sorbitan monooleate)), and the like. High-molecular-weight polyethylene glycols include those having molecular weights from 400 to 8000, such as PEG 400, PEG 1000, PEG 3350, PEG 5000, and PEG 8000. An exemplary high-molecular-weight polyethylene glycol is PEG 3350. The preferred concentration of PEG 3350 is 0.1-1%. Although 0.03% PEG 3350 effectively inhibits adsorptive losses and shear-induced aggregation/precipitation, somewhat higher concentrations will commonly be used in the initial formulation to account for dilution following reconstitution. For example, a typical unit dose of thrombin can be prepared by filling a vial with 1.6 mL of a 1.0 mg/mL (3200 U/mg) solution (about 5000 NIH U/vial) and lyophilizing. The lyophilized product, when reconstituted with 5 mL of normal saline, provides a thrombin concentration of about 1000 NIH U/mL (0.32 mg/mL). If the concentration of PEG 3350 in the initial formulation is 0.1%, the concentration in the reconstituted product will be 0.03%.

Within certain embodiments of the invention, $CaCl_2$ is included in the formulation to promote hemostasis, as it is required to activate several blood clotting factors (e.g., Factor IX, Factor X). When included, the concentration of $CaCl_2$ in the formulation is up to 5 mM, generally 1-5 mM, commonly 4 mM. Inclusion of calcium chloride may also improve the physical stability of thrombin.

For long-term storage, the aqueous solution is aliquoted into sterile vials, ampoules, or other containers and lyophilized according to procedures known in the art. The lyophilized product appears as a powder or cake, a cake being the preferred form. The containers are then sealed. It is preferred to use a seal that permits later injection of diluent through the seal and into the container. The container is labeled according to standard practice in the pharmaceutical field.

In one embodiment of the invention, the container is provided in a kit with a second container containing a diluent. Suitable diluents include normal saline for injection and water for injection. The kit may further comprise an application device, such as a sprayer, syringe, or the like.

For use, the lyophilized thrombin composition is reconstituted with a suitable diluent to the desired concentration, generally from about 100 NIH U/ml to about 5,000 NIH U/ml, typically about 1,000 NIH U/ml, although the actual concentration will be determined by the physician according to the needs of the individual patient. The thrombin can be applied to bleeding tissue to achieve hemostasis, often in combination with an absorbable gelatin sponge. The thrombin can also be used as a component of a tissue adhesive or fibrin glue. These and other uses of thrombin are known in the art.

The invention is further illustrated by the following non-limiting examples.

EXAMPLES

Example 1

Recombinant human thrombin (rhThrombin) was formulated at 1 mg/ml in 5 mM histidine, 150 mM NaCl, 4 mM $CaCl_2$, 0.1% PEG3350, pH 6.0 with varying concentrations of mannitol and sucrose as shown in Table 2.

TABLE 2

| Formulation | Mannitol | Sucrose |
|---|---|---|
| T | 5% | 0.5% |
| A | 5% | 1% |
| B | 5% | 2% |
| C | 5% | 3% |
| D | 4% | 3% |
| E | 3% | 3% |
| F | — | 5% |

1.6-ml aliquots of the solutions were placed in vials and lyophilized under the conditions shown in Table 3. For subsequent analysis, lyophilized samples were reconstituted with water where necessary. Visual observations of lyophilized and reconstituted samples are shown in Table 4.

TABLE 3

| Formulation | Freezing & Annealing | Primary Drying | Secondary Drying |
|---|---|---|---|
| T | 0.5° C./min to 5° C., hold 0.5 hr<br>0.25° C./min to −50° C., hold 2 hr<br>0.25° C./min to −30° C., hold 3 hr<br>0.25° C./min to −50° C., hold 2 hr | 0.5° C./min to −10° C., hold 16 hr<br>60 mTorr | 0.2° C./min to 30° C., hold 24 hr<br>60 mTorr |
| A, B, C, D, E, F | 0.5° C./min to 5° C., hold 2 hr<br>0.5° C./min to −50° C., hold 2 hr<br>0.25° C./min to −20° C., hold 2 hr<br>0.25° C./min to −25° C., hold 2 hr<br>0.25° C./min to −50° C., hold 2 hr | 0.5° C./min to −30° C., hold 10 hr<br>0.5° C./min to −25° C., hold 10 hr<br>0.5° C./min to −20° C., hold 10 hr<br>0.5° C./min to −15° C., hold 10 hr<br>60 mTorr | 0.5° C./min to 25° C., hold 24 hr<br>0.5° C./min to 30° C., hold 8 hr<br>0.5° C./min to 20° C., hold 6 hr<br>60 mTorr |

TABLE 4

| Formulation | Lyophilized Solid | Reconstituted Solution |
|---|---|---|
| T | White cake | Clear |
| A | White cake | Clear |
| B | White cake | Clear |
| C | White cake | Clear |
| D | White cake | Clear |
| E | White semi-collapsed cake or white powder | Clear |
| F | White powder | Clear |

Example 2

Formulations A, B, C, D, E, and F of rhThrombin were analyzed for the presence of aggregates/precipitants in solution. Pre- and post-lyophilization samples were analyzed by Right Angle Light Scattering (RALS) using a continuous spectrofluorometer (QUANTAMASTER QM4, Photon Technology International, Inc., Lawrenceville, N.J.). The excitation and emission wavelengths were both set to 320 nm. Samples were loaded in a quartz vial of 1-cm pathlength. The slit widths were adjusted to 2 nm, and signals were collected at 1 point/sec for 60 seconds. The applied current was 75 watts. The reported values (see FIG. 1) were the average counts recorded over 60 seconds. Significant light scattering consistent with aggregation/precipitation after reconstitution was found in Formulation A. Formulations E and F did not produce an acceptable cake upon lyophilization.

Example 3

Recovery of rhThrombin after lyophilization was measured using reverse-phase chromatography (RP-HPLC). Size-exclusion chromatography (SE-HPLC) was used to determine the percentage of soluble aggregate in test samples. Formulations A, B, C, D, E, and F were analyzed prior to lyophilization and after lyophilization and reconstitution.

For RP-HPLC, test samples and reference standard (rhThrombin, 1 mg/mL in dilution buffer (20 mM sodium phosphate, 140 mM NaCl, pH 7.0)) were filtered using centrifugal filter units (0.22 μm) (SPIN-X; Corning Life Sciences, Action, Mass.) at 14,000 RPM (20,800 RCF). A standard curve range from 5 to 40 μg was employed with samples injected at approximately 90% of the upper limit of quantification. Purity values were determined based on the area of the main peak relative to the total integrated peak area. Analysis was performed using an HPLC system (1100 Series; Agilent Technologies, Palo Alto, Calif.) configured with:

Binary pump with seal wash kit (G1312A)
Four channel solvent degasser (G1322A)
Thermostatted autosampler (G1329A/G1330A)
Extended volume upgrade kit utilizing a 900 μL syringe (G1363A)
Thermostatted column compartment with two heat exchangers (G1316A)
Column switching upgrade kit (G1353A)
Diode-array detector (G1315B) with 10 mm/13 μL flow cell
Agilent CHEMSTATION Software (Revision A.08.03)

For SE-HPLC, test samples and reference standard were filtered using centrifugal filter units (0.22 μm) at 14,000 RPM (20,800 RCF). A standard curve range from 5.1 to 102 μg was utilized, with samples injected at approximately 90% of the upper limit of quantification. The percentage of aggregates was determined based on the area of the detected peaks preceding the main rhThrombin peak relative to the total integrated peak area. Analysis was performed using an HPLC system as disclosed above.

These analyses showed an increase in recovery of rhThrombin after lyophilization with increasing sucrose (≧3%) content as shown in Tables 5 and 6. Data are presented as rhThrombin concentration (mg/ml). The observation that increases in soluble aggregate did not necessarily correlate with lower recovery is consistent with the formation of insoluble rhThrombin aggregate during lyophilization.

TABLE 5

| | RP-HPLC | | | | | |
|---|---|---|---|---|---|---|
| Formulation: | A | B | C | D | E | F |
| Pre-lyophilization: | 1.03 | 1.06 | 1.02 | 1.04 | 1.03 | 1.04 |
| Reconstituted: | 0.91 | 0.92 | 0.93 | 0.94 | 0.96 | 0.96 |
| % Recovered | 88.3% | 86.8% | 91.2% | 90.4% | 93.2% | 92.3% |

TABLE 6

| | % soluble aggregate by SE-HPLC | | | | | |
|---|---|---|---|---|---|---|
| Formulation | A | B | C | D | E | F |
| Pre-lyophilization | 0.5 | 0.5 | 0.5 | 0.5 | 0.6 | 0.6 |
| Post-lyophilization | 0.6 | 0.7 | 0.7 | 0.7 | 0.5 | 0.5 |

Example 4

Storage stability of rhThrombin formulations was studied over a 6-month period. Lyophilized samples of formulations A, B, C, D, E, and F were stored at 40° C. and at 25° C. and analyzed for content (thrombin concentration) by RP-HPLC at 0, 1, 2, 3, and 6 months as disclosed above. At both temperatures, formulation A, upon reconstitution, became turbid after two months (Table 7). Formulations E and F produced unacceptable cakes and were not analyzed after the 0-month time point. Stability, expressed as % recovery, is shown in Tables 8 and 9.

TABLE 7

| Temperature | Time | T | A | B | C | D |
|---|---|---|---|---|---|---|
| −20° C. | 0 | Clear | Clear | Clear | Clear | Clear |
| | 1 month | Clear | Clear | Clear | Clear | Clear |
| | 2 months | Clear | Clear | Clear | Clear | Clear |
| | 3 months | Clear | Clear | Clear | Clear | Clear |
| | 6 months | Clear | Clear | Clear | Clear | Clear |
| 5° C. | 1 week | Slightly turbid | Clear | Clear | Clear | Clear |
| | 2 week | Clear | Clear | Clear | Clear | Clear |
| | 1 month | Clear | Clear | Clear | Clear | Clear |
| | 2 months | Clear | Clear | Clear | Clear | Clear |
| | 3 months | Clear | Clear | Clear | Clear | Clear |
| | 6 months | Clear | Clear | Clear | Clear | Clear |
| 25° C. | 1 week | Slightly turbid | Clear | Clear | Clear | Clear |
| | 2 week | Slightly turbid | Clear | Clear | Clear | Clear |
| | 1 month | Slightly turbid | Clear | Clear | Clear | Clear |
| | 2 months | Clear | Slightly turbid | Clear | Clear | Clear |
| | 3 months | Slightly turbid | Slightly turbid | Clear | Clear | Clear |
| | 6 months | Clear | Slightly turbid | Clear | Clear | Clear |
| 40° C. | 1 week | Slightly turbid | Not tested | Not tested | Not tested | Not tested |
| | 2 week | Slightly turbid | Not tested | Not tested | Not tested | Not tested |
| | 1 month | Slightly turbid | Clear | Clear | Clear | Clear |
| | 2 months | Not tested | Slightly turbid | Clear | Clear | Clear |
| | 3 months | Not tested | Slightly turbid | Clear | Clear | Clear |
| | 6 months | Not tested | Slightly turbid | Clear | Clear | Clear |

TABLE 8

% recovery of thrombin during storage at 40° C.

| Formulation | Months | | | | | | |
|---|---|---|---|---|---|---|---|
| | 0 | 0.25 | 0.5 | 1 | 2 | 3 | 6 |
| T | 100 | 87.5 | 83.3 | 84.4 | n.t. | nt. | nt. |
| A | 100 | n.t. | n.t. | 95.6 | 94.5 | 92.3 | 90.1 |
| B | 100 | n.t. | n.t. | 96.7 | 98.9 | 95.7 | 92.4 |
| C | 100 | n.t. | n.t. | 96.8 | 95.7 | 93.5 | 91.4 |
| D | 100 | n.t. | n.t. | 97.9 | 97.9 | 95.7 | 93.6 | n.t. = not tested.

TABLE 9

% recovery of thrombin during storage at 25° C.

| Formulation | Months | | | | | |
|---|---|---|---|---|---|---|
| | 0 | 1 | 2 | 3 | 6 | 12 |
| Tox | 100 | 97.9 | 93.8 | 94.8 | 94.8 | 93.4 |
| A | 100 | 101 | 98.9 | 98.9 | 95.6 | 96.7 |
| B | 100 | 100 | 100 | 97.8 | 95.7 | 97.8 |
| C | 100 | 98.9 | 100 | 96.8 | n.t. | 100 |
| D | 100 | 98.9 | 98.9 | 97.9 | 97.9 | 97.9 |

*n.t. = not tested.

Example 5

Lyophilized samples of formulations A, B, C, D, E, and F were stored at 40° C. and at 25° C. and analyzed at 0, 1, 2, 3, and 6 months for the presence of high molecular weight impurities (soluble aggregate) by SE-HPLC as disclosed above. Results, shown in Table 10, indicated that in formulation T (containing the least amount of sucrose), increases in soluble aggregate were detected after one week. However, in formulations containing 1% or more sucrose, significant increases were not found after six months. Formulations E and F produced unacceptable cakes and were not analyzed after the O-month time point.

TABLE 10

% aggregates; storage at 40° C.

| Formulation | Months | | | | | | |
|---|---|---|---|---|---|---|---|
| | 0 | 0.25 | 0.5 | 1 | 2 | 3 | 6 |
| T | 0.3 | 1.1 | 1.1 | 1.1 | n.t | n.t. | n.t. |
| A | 0.6 | n.t. | n.t. | 0.7 | 0.8 | 0.6 | 0.8 |
| B | 0.7 | n.t. | n.t. | 0.6 | 0.6 | 0.5 | 0.9 |
| C | 0.7 | n.t. | n.t. | 0.6 | 0.6 | 0.6 | 0.6 |
| D | 0.7 | n.t. | n.t. | 0.6 | 0.6 | 0.6 | 0.7 | n.t. = not tested.

TABLE 11

% aggregates; storage at 25° C.

| Formulation | Months | | | | | |
|---|---|---|---|---|---|---|
| | 0 | 1 | 2 | 3 | 6 | 12 |
| T | 0.3 | 0.4 | 0.5 | 0.5 | 0.7 | 0.5 |
| A | 0.6 | 0.5 | 0.5 | 0.5 | 0.6 | 0.6 |
| B | 0.7 | 0.8 | 0.7 | 0.6 | 0.8 | 0.6 |

TABLE 11-continued

% aggregates; storage at 25° C.

| Formulation | Months | | | | | |
|---|---|---|---|---|---|---|
| | 0 | 1 | 2 | 3 | 6 | 12 |
| C | 0.7 | 0.8 | 0.8 | 0.6 | 0.6 | 0.6 |
| D | 0.7 | 0.7 | 0.6 | 0.6 | 0.7 | 0.6 |

Example 6

Figure 2:
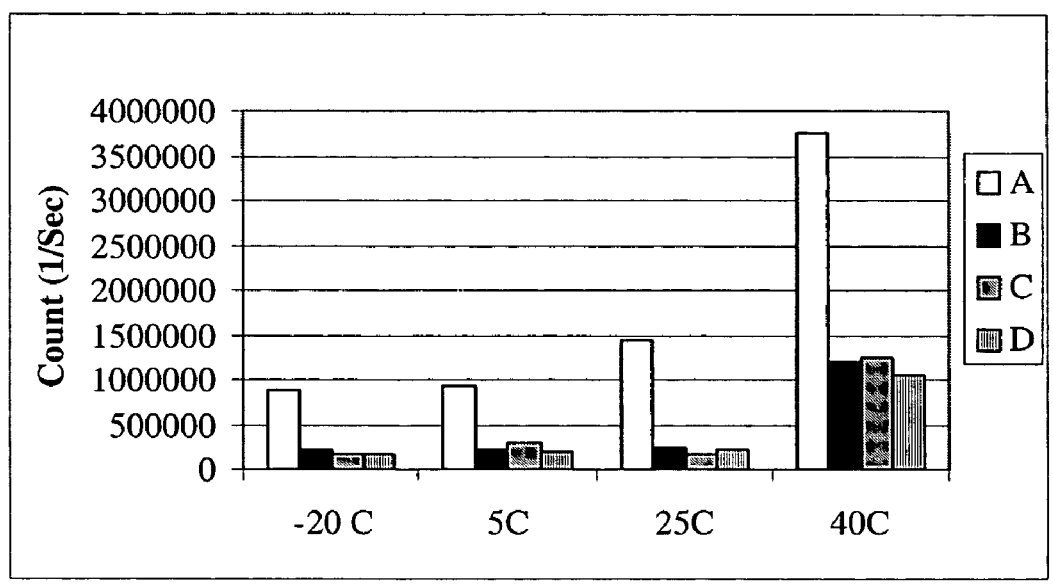
FIG. 2 illustrates the analysis of certain thrombin formulations by RALS following storage for thirteen weeks.
Figure 3:
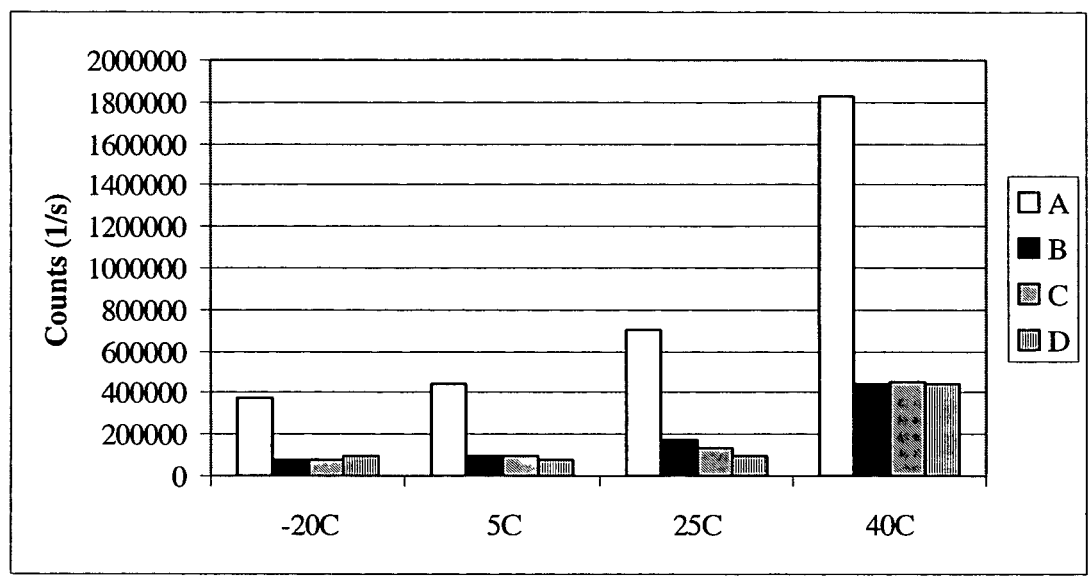
FIG. 3 illustrates the analysis of certain thrombin formulations by RALS following storage for six months.

Lyophilized samples of formulations A, B, C, and D were stored for thirteen weeks and six months at −20° C., 5° C., 25° C. and 40° C., then analyzed for RALS as disclosed in Example 2, above. Increases in light scattering measured by RALS are associated with the presence of insolubles and/or soluble aggregates. Results, shown in Tables 12 and 13 (as counts per second), and presented graphically in FIGS. 2 and 3, indicated that Formulations B, C, and D were more stable than Formulation A with respect to aggregation during storage under all test conditions. Due to minor instrument variations between the 13-week and 6-month time points, the absolute numbers of two time points should not be compared; the RALS data should be compared only among the formulations tested at same time.

TABLE 12

13 weeks

| Storage Temperature | Formulation | | | |
|---|---|---|---|---|
| | A | B | C | D |
| −20° C. | 870,148.3 | 220,321.1 | 174,001.5 | 175,358.3 |
| 5° C. | 917,635.8 | 209,274.9 | 298,378.7 | 183,227.1 |
| 25° C. | 1,442,075 | 243,777.1 | 160,173.6 | 211,948.2 |
| 40° C. | 3,746,816 | 1,196,508 | 1,245,188 | 1,049,673 |

TABLE 13

6 Months

| Storage Temperature | Formulation | | | |
|---|---|---|---|---|
| | A | B | C | D |
| −20 C. | 377158.2 | 72443.12 | 74719.25 | 92018.51 |
| 5 C | 438323.8 | 100675.1 | 100185.1 | 76518.18 |
| 25 C | 705247.2 | 175997.6 | 134422.6 | 92118.5 |
| 40 C | 1824263 | 438520.7 | 455521.4 | 446050.9 |

Example 7

Figure 4:
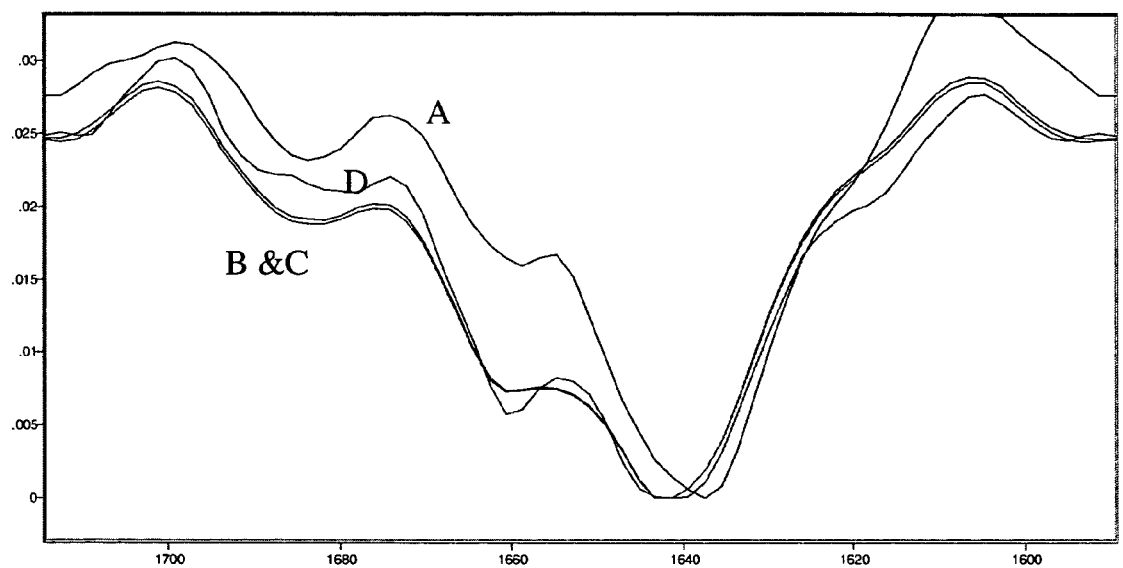
FIG. 4 illustrates the analysis of thrombin secondary structure by Fourier transform infrared spectroscopy using four formulations of recombinant human thrombin (labeled A, B, C, and D).

Lyophilized samples of formulations A, B, C, and D were analyzed by Fourier transform infrared (FTIR) spectroscopy to compare the secondary structure of rhThrombin in the lyophilized state. Infrared spectra were obtained with a FTIR spectrometer (FTLA2000-104, ABB Inc., Norwalk, Conn.). The lyophilized samples were mixed with potassium bromide (KBr) (approximate ratio 1:100 rhThrombin:KBr) and pressed to form pellets. The spectra were collected in single-beam transmission mode. To reduce the interferences from excipients and water vapor, the spectra of placebo and water vapor were subtracted from the protein spectra using analytical software (BOMEN-GRAMS/32 Al (Version 6.01); ABB Inc.). The second derivative spectra were created using the Savitzky-Golay function of second degree. The rhThrombin formulations were compared in the amide I region (1700-1600 cm$^{-1}$). As shown in FIG. 4, similar spectra were obtained for formulations B, C, and D, with formulation A giving a different spectrum.

Three replicates of formulation A were then tested by FTIR as disclosed above. The resulting spectra were essentially identical.

Figure 5:
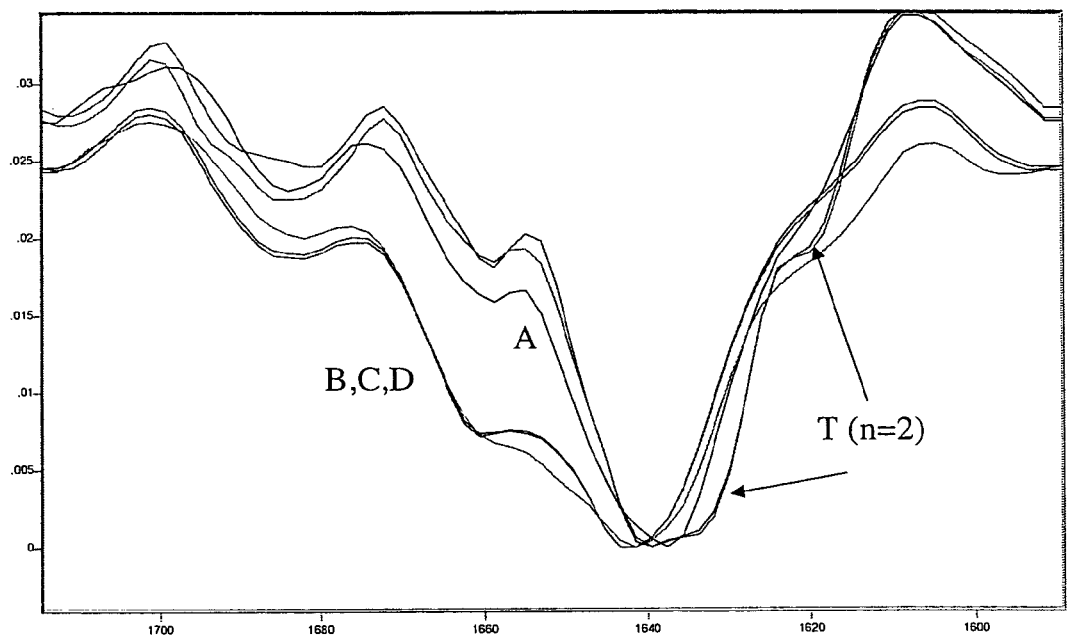
FIG. 5 illustrates the analysis of thrombin secondary structure by Fourier transform infrared spectroscopy using five formulations of recombinant human thrombin (labeled T, A, B, C, and D).

Formulations A, B, C, and D were then compared to a formulation containing 5% mannitol and 0.5% sucrose (Formulation T). FTIR was carried out as disclosed above. As shown in FIG. 5, Formulations B, C, and D gave similar spectra, while the spectra of formulations containing 5% mannitol and either 1% sucrose or 0.5% sucrose indicated a different spectra. The increases in RALS observed after lyophilization when formulations containing $\leq$1% sucrose are compared to those containing $\geq$2% sucrose are consistent with these findings (Example 6). These data suggest that thrombin is partially unfolded in formulations containing $\leq$1% sucrose (leading to increased insolubles upon reconstitution), whereas, the secondary structure of thrombin is stabilized in the presence of $\geq$2% sucrose during lyophilization.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A composition consisting essentially of:
   0.1 mg/mL to 5.0 mg/mL thrombin;
   2% to 4% (w/v) sucrose;
   3.5% to 5% (w/v) mannitol;
   50 mM to 300 mM NaCt;
   0-5 mM CaCl2;
   0.03% to 1% (w/v) of a surfactant or high-molecular-weight polyethylene glycol; and
   a physiologically acceptable buffer,
   in aqueous solution at pH 5.7-7.4, wherein concentration of the buffer is selected to provide approximately physiological pH upon application of the composition in a surgical setting;
   wherein the ratio of mannitol:sucrose is greater than 1:1 but not greater than 2.5:1 (w/w) and wherein the molar ratio of sucrose:thrombin is at least 700:1.

2. The composition of claim 1, wherein the ratio of mannitol:sucrose is 1.33:1 (w/w).

3. The composition of claim 1, wherein the molar ratio of sucrose:thrombin is at least 2000:1.

4. The composition of claim 1, wherein the thrombin is human thrombin.

5. The composition of claim 1, wherein the thrombin is recombinant human thrombin.

6. The composition of claim 1, wherein the thrombin concentration is 0.5-3.0 mg/ml.

7. The composition of claim 1, wherein the thrombin concentration is 1 mg/ml.

8. The composition of claim 1, wherein the sucrose concentration is 3% (w/v).

9. The composition of claim 1, wherein the mannitol concentration is 4% (w/v).

10. The composition of claim 1, wherein the sucrose concentration is 3% (w/v) and the mannitol concentration is 4% (w/v).

11. The composition of claim 1, wherein the surfactant or high-molecular-weight polyethylene glycol is PEG 3350.

12. The composition of claim 11, wherein the concentration of PEG 3350 is 0.1% (w/v).

13. The composition of claim 1, wherein the pH is 6.0.

14. The composition of claim 1, wherein the buffer is selected from the group consisting of histidine, citrate, phosphate, Tris, and succinate buffers.

15. The composition of claim 1, wherein the buffer is histidine buffer.

16. The composition of claim 1, wherein the histidine buffer concentration is 2.0-10 mM.

17. The composition of claim 1, wherein the buffer is 5 mM histidine at pH 6.0.

18. The composition of claim 1, consisting essentially of:
    0.1 mg/mL to 5.0 mg/mL thrombin;
    2% to 4% (w/v) sucrose;
    3.5% to 5% (w/v) mannitol;
    100 mM to 200 mM NaCl;
    1 mM to 5 mM CaCl$_2$;
    0.03% to 1% (w/v) PEG3350; and
    2 mM to 10 mM histidine
in aqueous solution at pH 5.5-6.5, wherein the ratio of mannitol:sucrose is greater than 1:1 but not greater than 2.5:1 (w/w).

19. The composition of claim 18, consisting essentially of:
    1 mg/ml thrombin;
    3% (w/v) sucrose;
    4% (w/v) mannitol;
    4 mM CaCl$_2$;
    0.1% (w/v) PEG33500;
    150 mM NaCl; and
    5 mM histidine
in aqueous solution at pH 6.0.

20. A method of preparing a lyophilized thrombin composition comprising:
    providing a composition according to claim 1; and
    lyophilizing the aqueous solution to form a lyophilized thrombin composition.

21. A lyophilized thrombin composition prepared by the method of claim 20.

22. The composition of claim 21, contained in a sealed container having a label affixed to an exterior surface thereof.

23. The composition of claim 22, which contains from 2,500 to 20,000 NIH units of thrombin.

24. A kit comprising the composition of claim 22 and a second sealed container containing a diluent.

25. The kit of claim 24, wherein the diluent is normal saline.

26. The kit of claim 24, further comprising an application device.

27. A method of preparing a lyophilized thrombin composition comprising:
    providing a composition according to claim 18; and
    lyophilizing the aqueous solution to form a lyophilized thrombin composition.

* * * * *